United States Patent
Melkent et al.

(10) Patent No.: US 9,433,453 B2
(45) Date of Patent: Sep. 6, 2016

(54) IMPLANT WITH AN INTERFERENCE FIT FASTENER

(71) Applicant: Warsaw Orthopedic, Inc., Warsaw, IN (US)

(72) Inventors: Anthony J. Melkent, Memphis, TN (US); Thomas A. Carls, Memphis, TN (US); Lindsey G. Waugh, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 46 days.

(21) Appl. No.: 14/751,939

(22) Filed: Jun. 26, 2015

(65) Prior Publication Data

US 2015/0289912 A1    Oct. 15, 2015

Related U.S. Application Data

(62) Division of application No. 12/508,669, filed on Jul. 24, 2009, now Pat. No. 9,095,444.

(51) Int. Cl.
*A61F 2/44* (2006.01)
*A61B 17/80* (2006.01)
(Continued)

(52) U.S. Cl.
CPC ....... *A61B 17/8052* (2013.01); *A61B 17/7059* (2013.01); *A61B 17/863* (2013.01); *A61B 17/8605* (2013.01); *A61B 17/8625* (2013.01); *A61F 2/4425* (2013.01); *A61F 2/4455* (2013.01); *A61B 2017/00955* (2013.01); *A61F 2/30749* (2013.01); *A61F 2/30965* (2013.01); *A61F 2002/30016* (2013.01); *A61F 2002/30517* (2013.01); *A61F 2002/30578* (2013.01); *A61F 2002/30649* (2013.01); *A61F 2002/30787* (2013.01); *A61F 2002/30794* (2013.01); *A61F 2002/4475* (2013.01); *A61F 2220/0008* (2013.01); *A61F 2220/0025* (2013.01); *A61F 2250/0019* (2013.01); *A61F 2310/00017* (2013.01); *A61F 2310/00023* (2013.01)

(58) Field of Classification Search
CPC .............................. A61B 17/8052; A61F 2/44
See application file for complete search history.

(56) References Cited

U.S. PATENT DOCUMENTS

| | | |
|---|---|---|
| 4,657,550 A | 4/1987 | Daher |
| 4,834,757 A | 5/1989 | Brantigan |

(Continued)

FOREIGN PATENT DOCUMENTS

| | | |
|---|---|---|
| EP | 1346697 A2 | 9/2003 |
| WO | 9535067 | 12/1995 |

*Primary Examiner* — Eduardo C Robert
*Assistant Examiner* — Nicholas Plionis

(57) ABSTRACT

An implant with an interference fit fastener for attaching the implant to a bone. The interference fit prevents backout of the fastener after the attachment. The implant may include a passage with a first end and second end. The passage may include a first interference section between the first and second ends. A fastener with an elongated shape may be sized to extend through the passage to attach the implant to the bone. The fastener may include a second interference section. During insertion of the fastener through the passage and into the bone, the second interference section of the fastener may contact against and modify or be modified by the first interference section of the passage. This modification may create the interference fit between the implant and the fastener that prevents backout. The interference sections may remain in contact or may move apart once the fastener is fully attached to the bone.

20 Claims, 11 Drawing Sheets

(51) Int. Cl.
  *A61B 17/86*  (2006.01)
  *A61B 17/70*  (2006.01)
  *A61F 2/30*   (2006.01)
  *A61B 17/00*  (2006.01)

(56) References Cited

U.S. PATENT DOCUMENTS

| | | |
|---|---|---|
| 4,878,915 A | 11/1989 | Brantigan |
| 4,904,261 A | 2/1990 | Dove |
| 4,955,908 A | 9/1990 | Frey |
| 5,019,079 A | 5/1991 | Ross |
| 5,041,113 A | 8/1991 | Biedermann |
| 5,053,036 A | 10/1991 | Perren |
| 5,067,956 A | 11/1991 | Buford |
| 5,085,548 A | 2/1992 | Moyles |
| 5,120,171 A | 6/1992 | Lasner |
| 5,127,912 A | 7/1992 | Ray |
| 5,147,363 A | 9/1992 | Harle |
| 5,180,381 A | 1/1993 | Aust |
| 5,180,382 A | 1/1993 | Frigg |
| 5,190,544 A | 3/1993 | Chapman |
| 5,192,327 A | 3/1993 | Brantigan |
| 5,217,462 A | 6/1993 | Asnis |
| 5,226,766 A | 7/1993 | Lasner |
| 5,234,430 A | 8/1993 | Huebner |
| 5,252,016 A | 10/1993 | Schmid |
| 5,259,398 A | 11/1993 | Vrespa |
| 5,290,312 A | 3/1994 | Kojimoto |
| 5,300,073 A | 4/1994 | Ray |
| 5,300,076 A | 4/1994 | Leriche |
| 5,306,275 A | 4/1994 | Bryan |
| 5,306,309 A | 4/1994 | Wagner |
| 5,338,197 A | 8/1994 | Kwan |
| 5,348,026 A | 9/1994 | Davidson |
| 5,360,452 A | 11/1994 | Engelhardt |
| 5,364,399 A | 11/1994 | Lowery |
| 5,364,400 A | 11/1994 | Rego |
| 5,397,363 A | 3/1995 | Gelbard |
| 5,403,136 A | 4/1995 | Mathys |
| 5,405,391 A | 4/1995 | Hednerson |
| 5,423,826 A | 6/1995 | Coates |
| 5,425,772 A | 6/1995 | Brantigan |
| 5,443,509 A | 8/1995 | Boucher |
| 5,443,514 A | 8/1995 | Steffee |
| 5,456,685 A | 10/1995 | Huebner |
| 5,470,334 A | 11/1995 | Ross |
| 5,484,440 A | 1/1996 | Allard |
| 5,492,442 A | 2/1996 | Lasner |
| 5,498,265 A | 3/1996 | Asnis |
| 5,514,180 A | 5/1996 | Heggeness |
| 5,520,690 A | 5/1996 | Errico |
| 5,527,314 A | 6/1996 | Brumfield |
| 5,531,554 A | 7/1996 | Jeanson |
| 5,531,746 A | 7/1996 | Errico |
| 5,536,127 A | 7/1996 | Pennig |
| 5,545,165 A | 8/1996 | Biedermann |
| 5,549,612 A | 8/1996 | Yapp |
| 5,549,683 A | 8/1996 | Bonutti |
| 5,562,663 A | 10/1996 | Wisnewski |
| 5,562,672 A | 10/1996 | Huebner |
| 5,569,252 A | 10/1996 | Justin |
| 5,571,139 A | 11/1996 | Jenkins |
| 5,571,190 A | 11/1996 | Ulrich |
| 5,578,034 A | 11/1996 | Estes |
| 5,601,553 A | 2/1997 | Trebing |
| 5,607,426 A | 3/1997 | Ralph |
| 5,628,740 A | 5/1997 | Mullane |
| 5,643,265 A | 7/1997 | Errico |
| 5,662,652 A | 9/1997 | Schafer |
| 5,665,087 A | 9/1997 | Huebner |
| 5,676,666 A | 10/1997 | Oxland |
| 5,676,703 A | 10/1997 | Gelbard |
| 5,692,497 A | 12/1997 | Schnitzer |
| 5,716,415 A | 2/1998 | Steffee |
| 5,727,943 A | 3/1998 | Beaty |
| 5,728,098 A | 3/1998 | Sherman |
| 5,730,744 A | 3/1998 | Justin |
| 5,735,653 A | 4/1998 | Schiefer |
| 5,735,853 A | 4/1998 | Olerud |
| 5,735,898 A | 4/1998 | Branemark |
| 5,743,912 A | 4/1998 | Lahille |
| 5,743,914 A | 4/1998 | Skiba |
| 5,746,039 A | 5/1998 | Nystrom |
| 5,766,252 A | 6/1998 | Henry |
| 5,766,254 A | 6/1998 | Gelbard |
| 5,779,704 A | 7/1998 | Kim |
| 5,810,821 A | 9/1998 | Vandewalle |
| 5,865,845 A | 2/1999 | Thalgott |
| 5,871,486 A | 2/1999 | Huebner |
| 5,876,402 A | 3/1999 | Errico |
| 5,876,446 A | 3/1999 | Agrawal |
| 5,888,224 A | 3/1999 | Beckers |
| 5,888,227 A | 3/1999 | Cottle |
| 5,904,683 A | 5/1999 | Pohndorf |
| 5,916,267 A | 6/1999 | Tienboon |
| 5,925,048 A | 7/1999 | Ahmad |
| 5,951,553 A | 9/1999 | Betz |
| 5,954,722 A | 9/1999 | Bono |
| 5,954,725 A | 9/1999 | Sherman |
| 5,961,524 A | 10/1999 | Crombie |
| 5,964,766 A | 10/1999 | Shaw |
| 5,964,768 A | 10/1999 | Huebner |
| 5,984,922 A | 11/1999 | McKay |
| 5,989,290 A | 11/1999 | Biedermann |
| 6,004,321 A | 12/1999 | Graser |
| 6,015,436 A | 1/2000 | Schonhoffer |
| 6,022,352 A | 2/2000 | Vandewalle |
| 6,030,162 A | 2/2000 | Huebner |
| 6,030,389 A | 2/2000 | Wagner |
| 6,039,740 A | 3/2000 | Olerud |
| 6,053,916 A | 4/2000 | Moore |
| 6,066,175 A | 5/2000 | Henderson |
| 6,074,393 A | 6/2000 | Sitoto |
| 6,077,267 A | 6/2000 | Huene |
| 6,086,613 A | 7/2000 | Camino |
| 6,090,143 A | 7/2000 | Meriwether |
| 6,106,557 A | 8/2000 | Robioneck |
| 6,117,173 A | 9/2000 | Taddia |
| 6,132,434 A | 10/2000 | Sherman |
| 6,158,245 A | 12/2000 | Savant |
| 6,159,211 A | 12/2000 | Boriani |
| 6,176,881 B1 | 1/2001 | Schar |
| 6,176,882 B1 | 1/2001 | Biedermann |
| 6,189,422 B1 | 2/2001 | Stihl |
| 6,193,721 B1 | 2/2001 | Michelson |
| 6,193,755 B1 | 2/2001 | Metz-Stavenhagen |
| 6,193,756 B1 | 2/2001 | Studer |
| 6,200,348 B1 | 3/2001 | Biedermann |
| 6,206,881 B1 | 3/2001 | Frigg et al. |
| 6,228,085 B1 | 5/2001 | Theken |
| 6,231,610 B1 | 5/2001 | Geisler |
| 6,235,034 B1 | 5/2001 | Bray |
| 6,235,059 B1 | 5/2001 | Benezech |
| 6,241,731 B1 | 6/2001 | Fiz |
| 6,245,108 B1 | 6/2001 | Biscup |
| 6,258,089 B1 | 7/2001 | Campbell |
| 6,261,291 B1 | 7/2001 | Talaber |
| 6,273,888 B1 | 8/2001 | Justis |
| 6,273,889 B1 | 8/2001 | Richelsoph |
| 6,277,149 B1 | 8/2001 | Boyle |
| 6,287,311 B1 | 9/2001 | Sherman |
| 6,290,711 B1 | 9/2001 | Caspari |
| 6,299,615 B1 | 10/2001 | Huebner |
| 6,322,562 B1 | 11/2001 | Wolter |
| 6,330,903 B1 | 12/2001 | Weinreich |
| 6,331,179 B1 | 12/2001 | Freid |
| 6,342,055 B1 | 1/2002 | Eisermann |
| 6,342,074 B1 | 1/2002 | Simpson |
| 6,355,043 B1 | 3/2002 | Adam |
| 6,375,657 B1 | 4/2002 | Doubler |
| 6,375,681 B1 | 4/2002 | Truscott |
| 6,383,186 B1 | 5/2002 | Michelson |
| 6,395,030 B1 | 5/2002 | Songer |
| 6,398,783 B1 | 6/2002 | Michelson |

(56) References Cited

U.S. PATENT DOCUMENTS

| | | |
|---|---|---|
| 6,398,786 B1 | 6/2002 | Sesic |
| 6,413,259 B1 | 7/2002 | Lyons |
| 6,416,528 B1 | 7/2002 | Michelson |
| 6,423,067 B1 | 7/2002 | Eisermann |
| 6,428,542 B1 | 8/2002 | Michelson |
| 6,428,575 B2 | 8/2002 | Koo |
| 6,440,136 B1 | 8/2002 | Gambale |
| 6,454,771 B1 | 9/2002 | Michelson |
| 6,454,773 B1 | 9/2002 | Sherman |
| 6,454,806 B1 | 9/2002 | Cohen |
| 6,458,159 B1 | 10/2002 | Thalgott |
| 6,468,277 B1 | 10/2002 | Justin |
| 6,481,760 B1 | 11/2002 | Noel |
| 6,482,233 B1 | 11/2002 | Aebi |
| 6,485,491 B1 | 11/2002 | Farris |
| 6,503,251 B1 | 1/2003 | Shadduck |
| 6,503,252 B2 | 1/2003 | Hansson |
| 6,503,279 B1 | 1/2003 | Webb |
| 6,513,814 B2 | 2/2003 | White |
| 6,520,993 B2 | 2/2003 | James |
| 6,527,776 B1 | 3/2003 | Michelson |
| 6,527,777 B2 | 3/2003 | Justin |
| 6,527,805 B2 | 3/2003 | Studer |
| 6,530,933 B1 | 3/2003 | Yeung |
| 6,533,786 B1 | 3/2003 | Needham |
| 6,551,323 B2 | 4/2003 | Doubler |
| 6,558,387 B2 | 5/2003 | Errico |
| 6,558,423 B1 | 5/2003 | Michelson |
| 6,562,039 B1 | 5/2003 | Wang |
| 6,565,573 B1 | 5/2003 | Ferrante |
| 6,579,290 B1 | 6/2003 | Hardcastle |
| 6,585,740 B2 | 7/2003 | Schlapfer |
| 6,592,586 B1 | 7/2003 | Michelson |
| 6,599,290 B2 | 7/2003 | Bailey |
| 6,602,255 B1 | 8/2003 | Campbell |
| 6,616,666 B1 | 9/2003 | Michelson |
| 6,620,163 B1 | 9/2003 | Michelson |
| 6,626,907 B2 | 9/2003 | Campbell |
| 6,629,998 B1 | 10/2003 | Lin |
| 6,635,086 B2 | 10/2003 | Lin |
| 6,660,004 B2 | 12/2003 | Barker |
| 6,666,638 B2 | 12/2003 | Craven |
| 6,666,870 B2 | 12/2003 | Dixon |
| 6,666,889 B1 | 12/2003 | Commarmond |
| 6,669,701 B2 | 12/2003 | Steiner |
| 6,673,075 B2 | 1/2004 | Santilli |
| 6,676,703 B2 | 1/2004 | Biscup |
| 6,682,561 B2 | 1/2004 | Songer |
| 6,695,845 B2 | 2/2004 | Dixon |
| 6,695,846 B2 | 2/2004 | Richelsoph |
| 6,706,046 B2 | 3/2004 | Orbay |
| 6,709,458 B2 | 3/2004 | Michelson |
| 6,712,818 B1 | 3/2004 | Michelson |
| 6,712,852 B1 | 3/2004 | Chung |
| 6,716,245 B2 | 4/2004 | Pasquet |
| 6,719,794 B2 | 4/2004 | Gerber |
| 6,730,091 B1 | 5/2004 | Pfefferle |
| 6,730,127 B2 | 5/2004 | Michelson |
| 6,736,816 B2 | 5/2004 | Ritland |
| 6,761,719 B2 | 7/2004 | Justis |
| 6,767,366 B2 | 7/2004 | Lee |
| 6,776,798 B2 | 8/2004 | Camino |
| 6,793,658 B2 | 9/2004 | LeHuec |
| 6,808,537 B2 | 10/2004 | Michelson |
| 6,808,538 B2 | 10/2004 | Paponneau |
| 6,814,756 B1 | 11/2004 | Michelson |
| 6,843,805 B2 | 1/2005 | Webb |
| 6,849,093 B2 | 2/2005 | Michelson |
| 6,852,126 B2 | 2/2005 | Ahlgren |
| 6,858,031 B2 | 2/2005 | Morrison |
| 6,875,215 B2 | 4/2005 | Taras |
| 6,887,243 B2 | 5/2005 | Culbert |
| 6,899,734 B2 | 5/2005 | Castro |
| 6,902,567 B2 | 6/2005 | Del Medico |
| 6,929,662 B1 | 8/2005 | Messerli |
| 6,941,635 B2 | 9/2005 | Craven |
| 6,953,463 B2 | 10/2005 | West |
| 6,955,677 B2 | 10/2005 | Dahners |
| 6,964,687 B1 | 11/2005 | Bernard |
| 6,974,480 B2 | 12/2005 | Messerli |
| 6,979,353 B2 | 12/2005 | Bresina |
| 6,984,234 B2 | 1/2006 | Bray |
| 6,984,235 B2 | 1/2006 | Huebner |
| 6,987,136 B2 | 1/2006 | Erbe |
| 6,989,014 B2 | 1/2006 | Justin |
| 7,014,659 B2 | 3/2006 | Boyer, II et al. |
| 7,037,309 B2 | 5/2006 | Weil |
| 7,044,702 B2 | 5/2006 | Ho |
| 7,044,953 B2 | 5/2006 | Capanni |
| 7,044,972 B2 | 5/2006 | Mathys |
| 7,052,499 B2 | 5/2006 | Steger |
| 7,063,701 B2 | 6/2006 | Michelson |
| 7,063,702 B2 | 6/2006 | Michelson |
| 7,070,601 B2 | 7/2006 | Culbert |
| 7,077,864 B2 | 7/2006 | Byrd |
| 7,094,239 B1 | 8/2006 | Michelson |
| 7,112,222 B2 | 9/2006 | Fraser |
| 7,122,037 B2 | 10/2006 | Happonen |
| 7,137,987 B2 | 11/2006 | Patterson |
| 7,137,997 B2 | 11/2006 | Paul |
| 7,141,068 B2 | 11/2006 | Ross |
| 7,163,561 B2 | 1/2007 | Michelson |
| 7,179,260 B2 | 2/2007 | Gerlach |
| 7,189,045 B2 | 3/2007 | McGovern |
| 7,192,447 B2 | 3/2007 | Rhoda |
| 7,223,292 B2 | 5/2007 | Messerli |
| 7,226,480 B2 | 6/2007 | Thalgott |
| 7,229,477 B2 | 6/2007 | Biscup |
| 7,232,464 B2 | 6/2007 | Mathieu |
| 7,235,078 B2 | 6/2007 | West |
| 7,235,079 B2 | 6/2007 | Jensen |
| 7,255,523 B2 | 8/2007 | Laan |
| 7,331,996 B2 | 2/2008 | Sato |
| 7,332,983 B2 | 2/2008 | Larson |
| 7,367,768 B2 | 5/2008 | McGovern |
| 7,473,256 B2 | 1/2009 | Assell |
| 7,491,221 B2 | 2/2009 | David |
| 7,517,350 B2 | 4/2009 | Weiner |
| 7,530,993 B2 | 5/2009 | Assell |
| 2001/0047172 A1 | 11/2001 | Foley |
| 2002/0099443 A1 | 7/2002 | Messerli |
| 2002/0111691 A1 | 8/2002 | Wang |
| 2002/0120273 A1 | 8/2002 | Needham |
| 2002/0128655 A1 | 9/2002 | Michelson |
| 2002/0183754 A1 | 12/2002 | Michelson |
| 2002/0183755 A1 | 12/2002 | Michelson |
| 2003/0018335 A1 | 1/2003 | Michelson |
| 2003/0028249 A1 | 2/2003 | Baccelli |
| 2003/0045880 A1 | 3/2003 | Michelson |
| 2003/0060828 A1 | 3/2003 | Michelson |
| 2003/0083746 A1 | 5/2003 | Kuslich |
| 2003/0093082 A1 | 5/2003 | Campbell |
| 2003/0105462 A1 | 6/2003 | Haider |
| 2003/0125739 A1 | 7/2003 | Bagga |
| 2003/0181912 A1 | 9/2003 | Michelson |
| 2003/0187440 A1 | 10/2003 | Richelsoph |
| 2003/0187442 A1 | 10/2003 | Richelsoph |
| 2003/0191471 A1 | 10/2003 | Michelson |
| 2003/0191472 A1 | 10/2003 | Michelson |
| 2003/0199980 A1 | 10/2003 | Siedler |
| 2003/0208204 A1 | 11/2003 | Bailey |
| 2004/0039383 A1 | 2/2004 | Jackson |
| 2004/0039387 A1 | 2/2004 | Gause |
| 2004/0087951 A1 | 5/2004 | Khalili |
| 2005/0033298 A1* | 2/2005 | Hawkes et al. .................. 606/61 |
| 2005/0085812 A1* | 4/2005 | Sherman et al. ................ 606/61 |
| 2005/0085910 A1 | 4/2005 | Sweeney |
| 2005/0085913 A1 | 4/2005 | Fraser |
| 2005/0113922 A1 | 5/2005 | Brazenor |
| 2005/0125029 A1 | 6/2005 | Bernard |
| 2005/0187552 A1 | 8/2005 | Michelson |
| 2005/0240268 A1 | 10/2005 | Messerli |
| 2006/0030851 A1 | 2/2006 | Bray |
| 2006/0085071 A1 | 4/2006 | Lechmann |

(56) References Cited

U.S. PATENT DOCUMENTS

| | | |
|---|---|---|
| 2006/0129151 A1 | 6/2006 | Allen |
| 2006/0167549 A1 | 7/2006 | Mathys |
| 2007/0088360 A1 | 4/2007 | Orbay et al. |
| 2007/0093901 A1 | 4/2007 | Grotz |
| 2007/0106384 A1 | 5/2007 | Bray |
| 2007/0162020 A1 | 7/2007 | Gerlach |
| 2007/0208423 A1 | 9/2007 | Messerli |
| 2007/0219635 A1 | 9/2007 | Mathieu |
| 2007/0233122 A1 | 10/2007 | Denis |
| 2007/0250167 A1 | 10/2007 | Bray |
| 2007/0276386 A1 | 11/2007 | Gerlach |
| 2007/0293948 A1 | 12/2007 | Bagga |
| 2008/0033440 A1 | 2/2008 | Moskowitz |
| 2008/0046090 A1 | 2/2008 | Paul |
| 2008/0177307 A1 | 7/2008 | Moskowitz |
| 2008/0183293 A1 | 7/2008 | Parry |
| 2008/0269806 A1 | 10/2008 | Zhang |
| 2008/0281425 A1 | 11/2008 | Thalgott |
| 2009/0024174 A1 | 1/2009 | Stark |
| 2009/0030520 A1 | 1/2009 | Biedermann |
| 2009/0105830 A1 | 4/2009 | Jones |
| 2009/0105831 A1 | 4/2009 | Jones |
| 2009/0118776 A1 | 5/2009 | Kelsch |
| 2009/0210067 A1* | 8/2009 | Meridew .................... 623/22.24 |
| 2010/0087925 A1* | 4/2010 | Kostuik et al. ............ 623/17.16 |

* cited by examiner

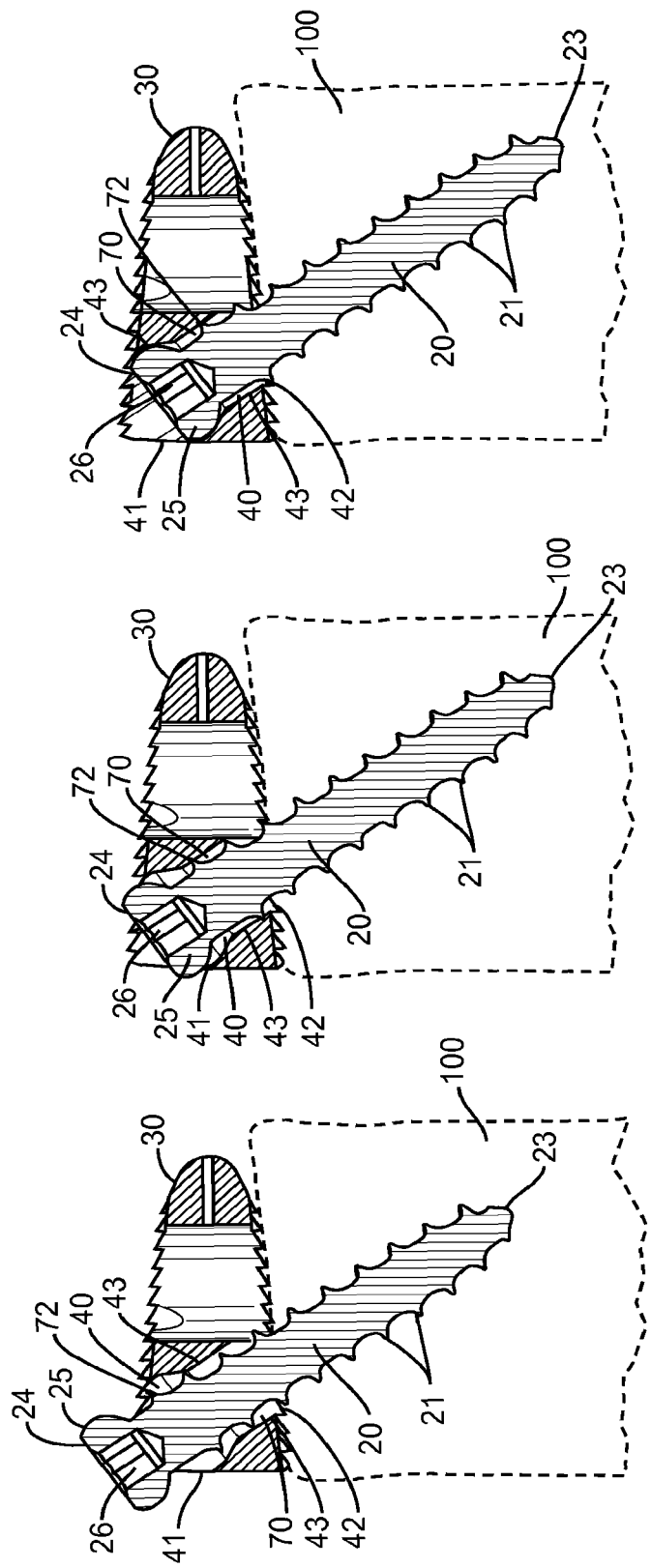

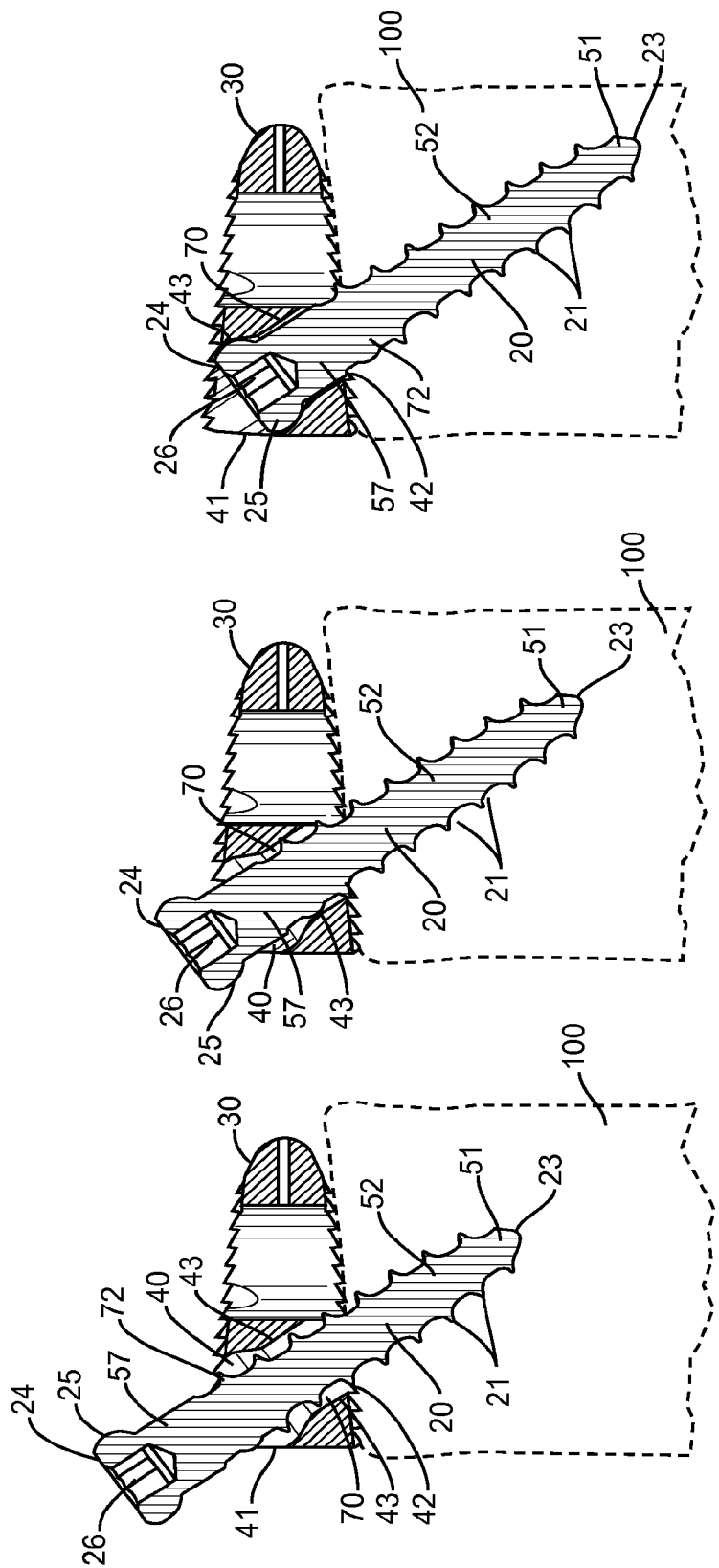

IMPLANT WITH AN INTERFERENCE FIT FASTENER

CROSS-REFERENCE TO RELATED APPLICATIONS

This application is a divisional application of U.S. patent application Ser. No. 12/508,669, filed Jul. 24, 2009, which is incorporated herein by reference, in its entirety.

BACKGROUND

The present application is directed to an implant attached to a bone with a fastener and, more particularly, to a fastener and an implant with different hardnesses with one being modified during insertion of the fastener through a passage in the implant to create an interference fit.

Various types of implants are inserted into a patient and attached with a fastener to a bone. The fastener extends through the implant and into the bone maintaining the implant against the bone. The fastener may also be configured to apply a compressive force against the implant. The implant and fastener should be structured to prevent the fastener from being non-threaded or otherwise removed from the bone and/or implant. This backward movement of the fastener relative to the bone and/or implant is referred to as backout. Backout may be caused by subsidence of the bone after attachment of the implant, or unthreading of the fastener from the bone.

Mechanisms have been developed to prevent backout of a fastener. One type of mechanism includes a snap ring that attaches to the implant and extends over a passage through the implant that receives the fastener. The snap ring is contacted during insertion of the fastener causing the snap ring to move away from the passage to allow insertion. Once the fastener passes, the snap-ring rebounds over the passage and head of the fastener. Drawbacks of these mechanisms include that the snap ring may become detached from the implant, and the snap ring may not rebound over the fastener. Further, a surgeon may have difficulty determining the position of the snap ring during a surgical procedure.

Another mechanism includes a projection that is movable by the surgeon between a locked orientation that extends over the passage in the implant and an unlocked orientation away from the passage. The projection is in the unlocked orientation when the fastener is inserted into the passage and driven into the bone. After insertion, the projection is moved by the surgeon to the locked orientation over the passage and the proximal end of the fastener. A drawback of this design is it requires the surgeon to perform an additional step after insertion of the fastener. It may also be difficult for a surgeon to determine that the projection is properly positioned over the fastener.

SUMMARY

The present application is an implant that attaches to a bone and methods of using the implant. The implant may include a passage with a first end and second end. The passage may include a first interference section between the first and second ends. A fastener with an elongated shape may be sized to extend through the passage to attach the implant to the bone. The fastener may include a second interference section. During insertion of the fastener through the passage and into the bone, the second interference section of the fastener may contact against and modify or be modified by the first interference section of the passage. This modification may create an interference fit between the implant and the fastener that prevents backout. The first and second interference sections may remain in contact once the fastener is fully attached to the bone, or may move apart.

The various aspects of the various embodiments may be used alone or in any combination, as is desired.

BRIEF DESCRIPTION OF THE DRAWINGS

FIG. 14 is a sectional view of a fastener inserted a first amount into a bone according to one embodiment.

FIG. 15 is a sectional view of a fastener inserted a second amount into a bone according to one embodiment.

FIG. 16 is a sectional view of a fastener inserted a third amount into a bone according to one embodiment.

FIG. 18 is a sectional view of a fastener inserted a first amount into a bone according to one embodiment.

FIG. 19 is a sectional view of a fastener inserted a second amount into a bone according to one embodiment.

FIG. 20 is a sectional view of a fastener inserted a third amount into a bone according to one embodiment.

DETAILED DESCRIPTION

The present application is directed to an implant with a self-locking bone fastener that attaches the implant to a bone. The implant includes a passage to receive the fastener. Sidewalls of the implant and the fastener include different hardnesses causing one to be modified when the fastener is inserted into the implant. The modification causes an interference fit between the fastener and implant to prevent backout of the fastener.

Figure 1:
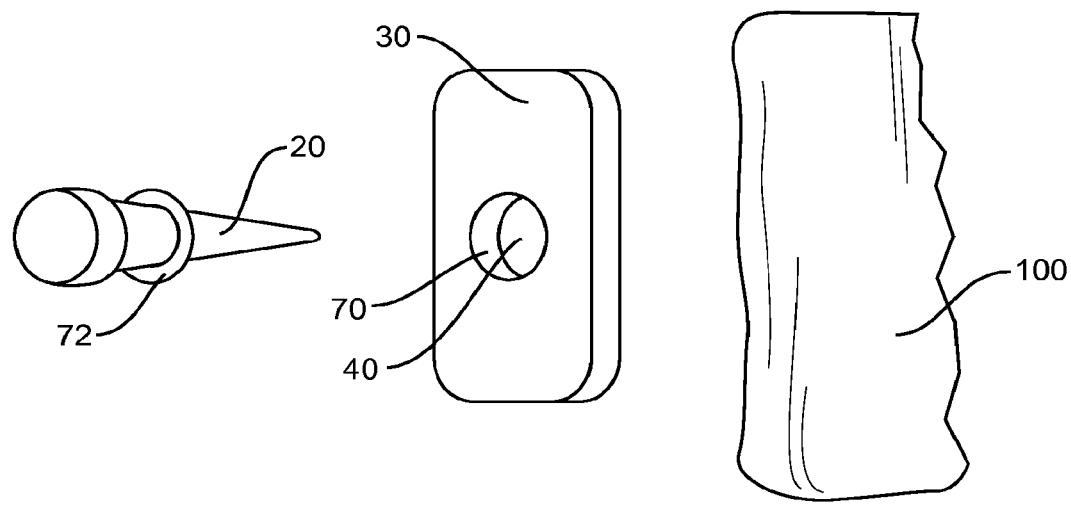
FIG. 1 is a schematic perspective view of a fastener and implant positioned at a bone according to one embodiment of the present application.

FIG. 1 schematically illustrates a fastener 20 sized to fit within a passage 40 in an implant 30. The fastener 20 functions to extend through the passage 40 and attach the implant 30 to the bone 100. The fastener 20 includes an interference section 72 with a larger diameter than an interference section 70 of the passage 40. The fastener 20 is also constructed of a material with a different hardness than the interference section 70. One of the interference sections 70, 72 is modified as the fastener 20 passes into the passage 40 and creates an interference fit. The interference fit at least prevents the fastener 20 from backing out of the bone 100 after attachment of the implant 30.

Figure 2:
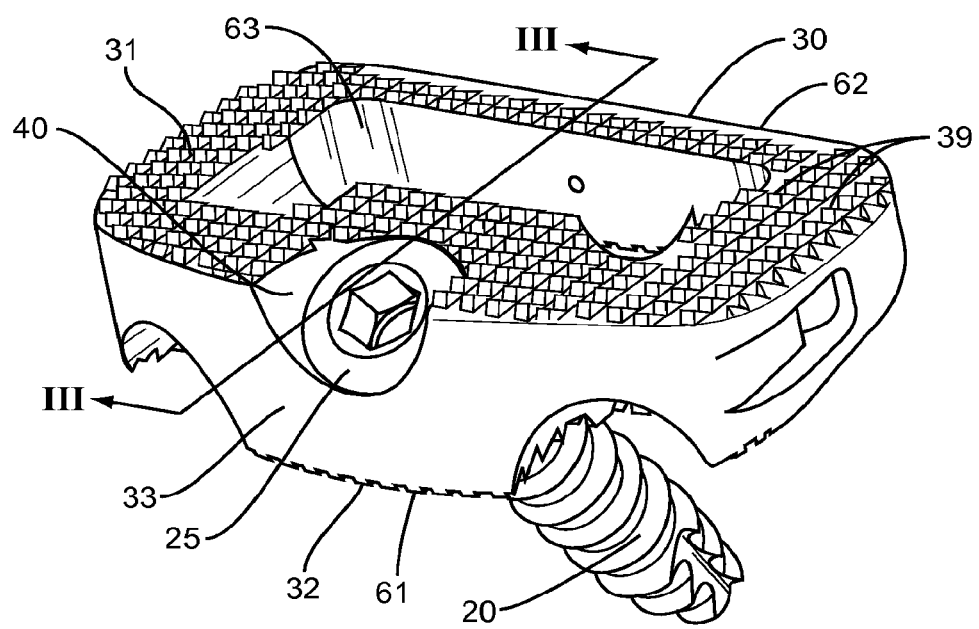
FIG. 2 is a perspective view of a fastener positioned in a passage through an implant according to one embodiment.
Figure 3:
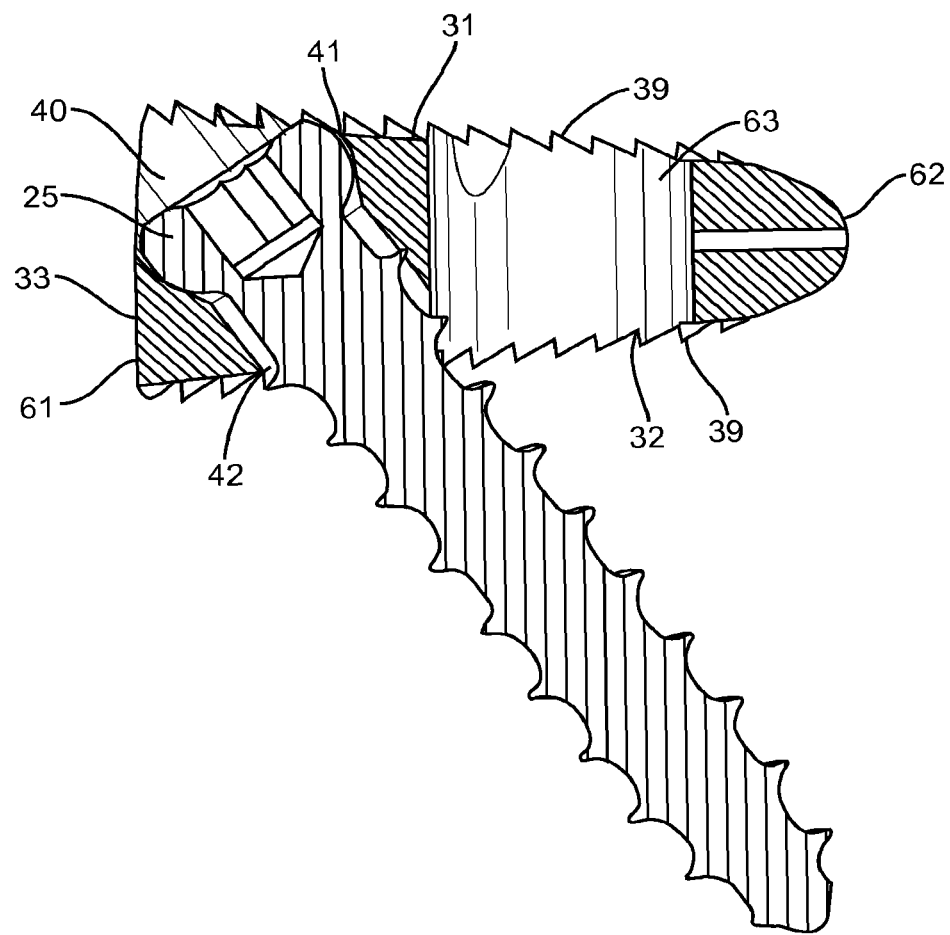
FIG. 3 is a sectional view cut along line III-III of FIG. 2.

The implant 30 is attached to the bone 100 by one or more fasteners 20 and may include a variety of shapes and configurations. FIGS. 2 and 3 include the implant 30 as a spacer configured to be positioned within an intervertebral space formed between vertebral members. The implant 30 includes a superior surface 31 configured to contact against a first vertebral member and an inferior surface 32 configured to contact against a second vertebral member. Teeth 39 may extend outward from one or both of the surfaces 31, 32 to facilitate insertion into the intervertebral space and/or maintain the position within the intervertebral space. A sidewall 33 extends between the surfaces 31, 32. The height of the spacer measured between the surfaces 31, 32 may be constant, or may vary as best illustrated in FIG. 3 with the height increasing from a first lateral sidewall 61 to a second lateral sidewall 62. A central passage 63 may extend through spacer and through the surfaces 31, 32.

Figure 4:
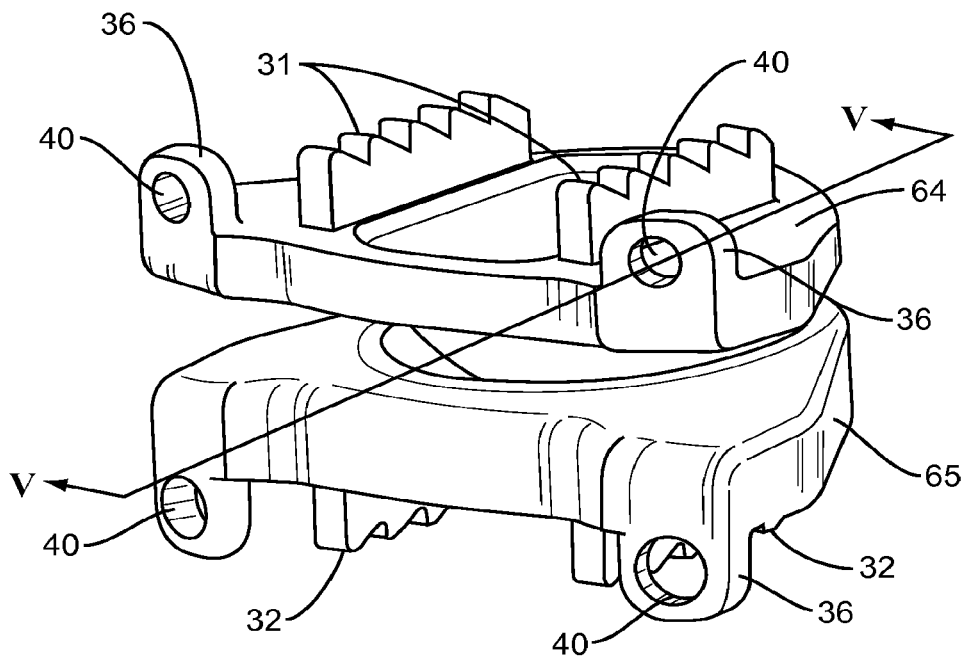
FIG. 4 is a perspective view of an implant according to one embodiment.
Figure 5:
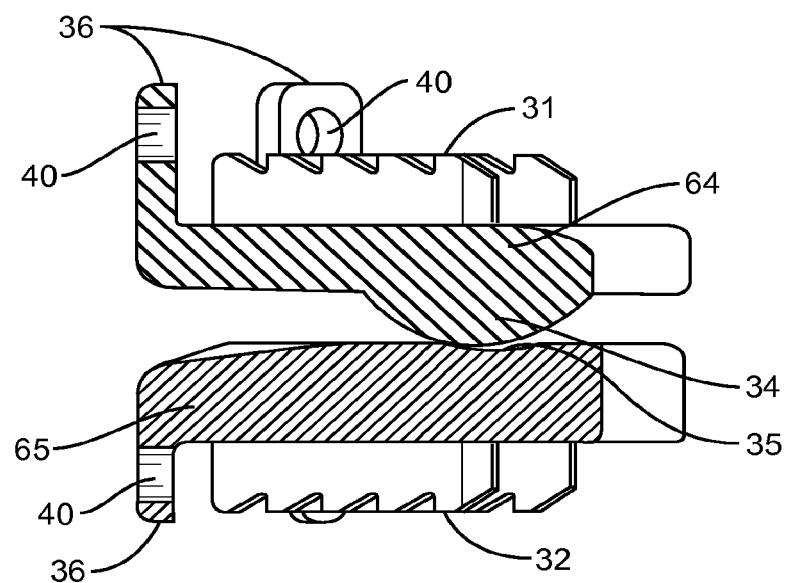
FIG. 5 is a sectional view cut along line V-V of FIG. 4.

Implant 30 may also include an artificial disc as illustrated in FIGS. 4 and 5. The implant 30 includes a first member 64 and a second member 65 configured to be positioned within the intervertebral space formed between vertebral members. The first member 64 includes a superior surface 31 configured to contact against the first vertebral member, and an inferior surface 32 is formed on a second member 65 to contact against the second vertebral member. The first member 64 also includes a convex section 34 that extends outward and mates with a concave section 35 in the second member 65. The convex and concave sections 34, 35 form a ball-and-socket arrangement that forms the artificial disc. Flanges 36 are positioned on the members 64, 65 and include passages 40 each sized to receive a fastener 20. Each of the flanges 36 and passages 40 may include different shapes, sizes, and orientations, or each may be substantially the same as best illustrated in FIG. 4. The passages 40 align with an exterior of the first and second vertebral members when the convex and concave sections 34, 35 are positioned within the intervertebral space. In another embodiment, the implant 30 does not include flanges 36 and the passages 40 extend directly through the first and second members 64, 65 in a similar manner as illustrated in FIGS. 2 and 3.

Figure 6:
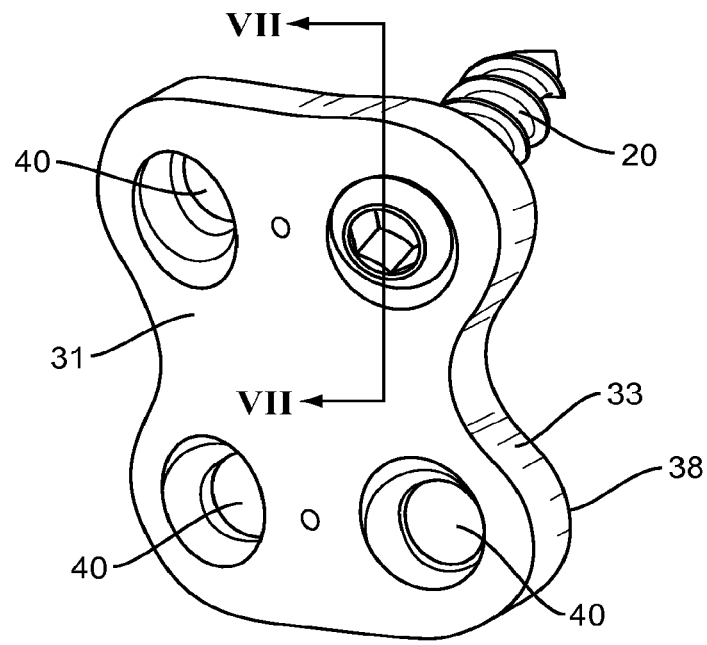
FIG. 6 is a perspective view of a fastener positioned in a passage through an implant according to one embodiment.
Figure 7:
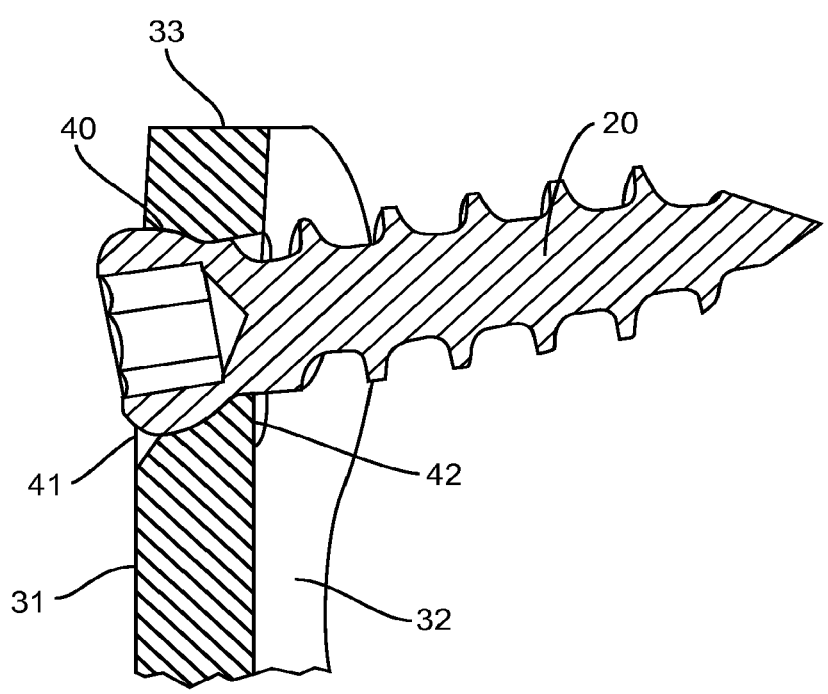
FIG. 7 is a sectional view cut along line VII-VII of FIG. 6.

Implant 30 may also include a plate as illustrated in FIGS. 6 and 7. The plate includes a first surface 31 that faces away from the bone 100 and a second surface 32 that faces towards and contacts against the bone 100. Sidewalls 33 extend between the first and second surfaces 31, 32. The plate may be substantially flat or may be curved. The thickness measured between the surfaces 31, 32 may be the same throughout the plate or may vary. One or more passages 40 extend through the plate from the first surface 31 to the second surface 32. One or more of the passages 40 may also be positioned at least partially through the sidewalls 33.

The implant 30 is constructed of a material with a different hardness than the fastener 20. This difference causes the implant 30 to modify or be modified by the fastener 20 during insertion and create an interference fit that prevents backout of the fastener 20. Implant materials include but are not limited to polyaryletherketone (PAEK), polyetheretherketone (PEEK), carbon-reinforced PEEK, polyetherketoneketone (PEKK), polysulfone, polyetherimide, polyimide, ultra-high molecular weight polyethylene (UHMWPE), plastics, titanium, titanium alloy, stainless steel, and metallic alloys.

Figure 8:
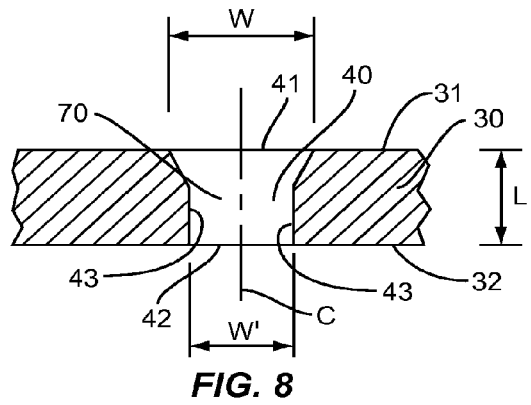
FIG. 8 is a sectional view of a passage through an implant according to one embodiment.
Figure 9:
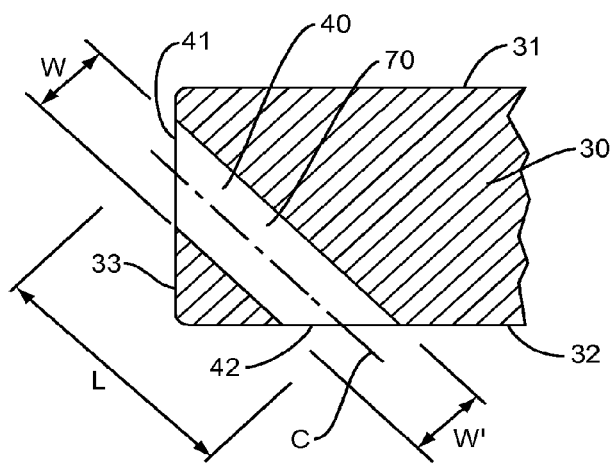
FIG. 9 is a sectional view of a passage through an implant according to one embodiment.

A passage 40 extends through the implant 30 to receive the fastener 20. As illustrated in FIG. 8, the passage 40 generally includes a first end 41 and a second end 42 with a length L measured along an axis C between the first and second ends 41, 42. Passage 40 further includes sidewalls 43 that extend between the ends 41, 42. A diameter W is measured across the passage 40 between the sidewalls 43. The diameter W may vary along the length L. FIG. 8 includes a diameter W that is wider at the first end 41 than the second end 42. The wider diameter W at the first end 41 forms a receptacle for seating a head 25 of the fastener 20 within the passage 40 as illustrated in FIGS. 2 and 3. FIG. 9 includes another passage 40 with a constant diameter W along the entire length L.

The passage 40 may extend through the implant 30 at various orientations. FIGS. 2 and 3 include the passage 40 angled relative to the superior and inferior surfaces 31, 32 with an axis neither parallel nor perpendicular to the surfaces 31, 32. The first end 41 extends through both the superior surface 31 and sidewall 33 and the second end 42 extends through the inferior surface 32. The amount of the angle relative to the superior and inferior surfaces 31, 32 may vary depending upon the context of use. Other configurations as illustrated in FIG. 9 include an angled orientation with the first end 41 of the passage 40 being isolated to just within the sidewall 33. FIGS. 4-7 include the passage 40 extending more directly through the implant 30 between opposing surfaces.

The passage 40 includes an interference section 70 that is interacts with the fastener 20 during insertion. In one embodiment as illustrated in FIG. 8, the interference section 70 includes a diameter W' that is narrower than the diameter W. The interference section 70 may include different shapes and lengths. FIG. 8 includes the interference section 70 extending along a limited distance of the length L, and specifically in proximity to the second surface 32. FIG. 9 includes the interference section 70 extending the entire length L of the passage 40 as the diameter W is constant along the length L (i.e., W equals W').

Figure 10:
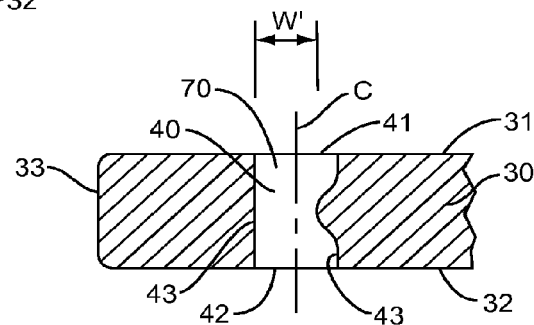
FIG. 10 is a sectional view of a passage through an implant according to one embodiment.
Figure 11:
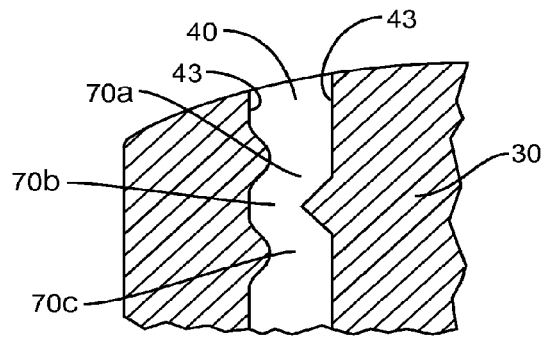
FIG. 11 is a sectional view of a passage through an implant according to one embodiment.

The interference section 70 may be symmetrical about the axis C. FIGS. 8 and 9 each include symmetrical interference sections 70. The interference section 70 may also include various other configurations. FIG. 10 includes an extension on one of the sidewalls 43 that forms the interference section 70. The passage 40 may also include multiple interference sections 70. FIG. 11 includes three interference sections 70a, 70b, 70c. The multiple sections 70 may each include the same or different shapes and/or diameters W'.

Figure 25:
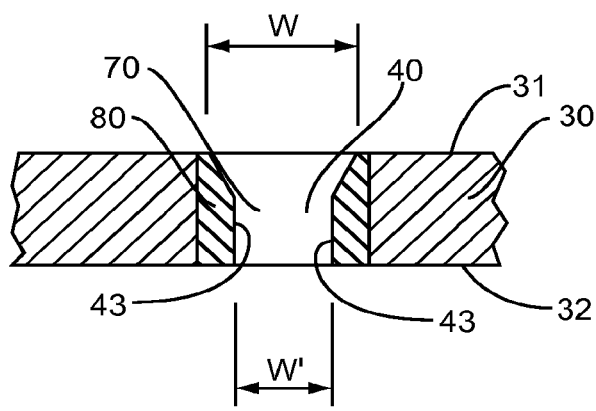
FIG. 25 is a sectional view of an insert attached to an implant according to one embodiment.
Figure 26:
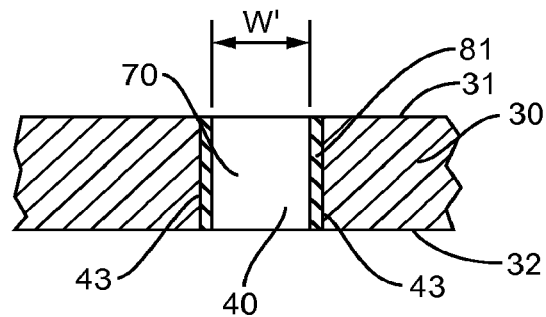
FIG. 26 is a sectional view of a coating applied to an implant according to one embodiment.

The interference section 70 includes a solid surface that engages the fastener 20. In one embodiment, the implant 30 includes a unitary one-piece construction. Therefore, the interference section 70 is constructed from the same material and from the same single structure as the remainder of the implant 30. In another embodiment as illustrated in FIG. 25, the interference section 70 is formed by an insert 80 that is attached to the implant 30. The insert 80 forms the passage 40 and the interference section 70. The insert 80 may be attached to the implant 30 in various manners, including but not limited to interference fit, thread fit, mechanical fasteners, and adhesive. Another embodiment includes a coating 81 applied to the sidewalls 43 of the passage 40 as illustrated in FIG. 26. The coating 81 reduces a width of the passage 40 and creates the interference section 70.

The passage 40 may include a circular shape when viewed along the axis C. However, passage 40 may also include other shapes including but not limited to oval, rectangular, square, and elliptical. The term diameter is used to define the distance across the passage 40 between the sidewalls 43 and should be construed in a manner to also apply to passages that are not circular.

The fastener 20 functions to extend through the passage 40 and attach the implant 30 to the bone 100. Fastener 20 may include various shapes and configurations to perform this function. Fastener 20 may be constructed from a variety of materials, including but not limited to titanium, titanium alloy, stainless steel, metallic alloys, polyaryletherketone (PAEK), polyetheretherketone (PEEK), carbon-reinforced PEEK, polyetherketoneketone (PEKK), polysulfone, polyetherimide, polyimide, ultra-high molecular weight polyethylene (UHMWPE), and plastics.

Figure 12:
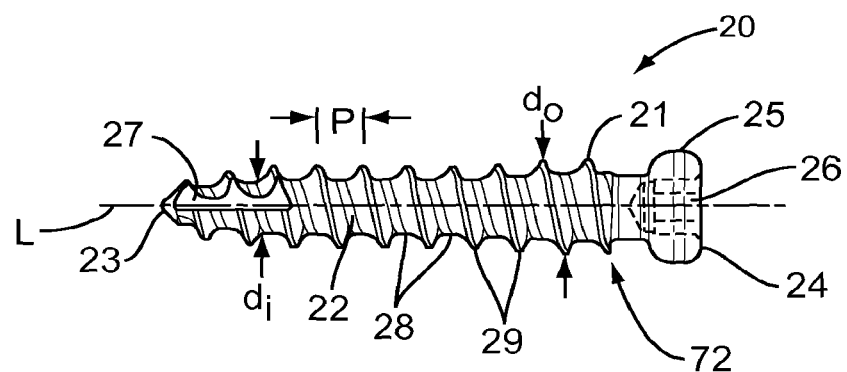
FIG. 12 is a side view of a fastener according to one embodiment.

FIG. 12 illustrates a fastener 20 with an elongated shape that extends along a longitudinal axis L and generally includes a shank 22 and a head 25. The fastener 20 includes a distal tip 23 at an end of the shank 22 and an opposing proximal end 24 at the head 25. The distal tip 23 is preferably tapered to a point to facilitate movement through the bone 100, although the tip 23 may include other non-tapered configurations. The length of the body 20 measured between the tip 23 and end 24 may vary.

The fastener 20 may include one or more helical threads 21 that wrap around the longitudinal axis and extend along the shank 22 and/or head 25. The thread 21 may extend along the entire length of the fastener 20, or just along a limited length. The thread 21 defines a root 28 in proximity to the longitudinal axis L and a crest 29 distanced from the longitudinal axis L. The fastener 20 includes a minor diameter di measured between the roots 28, and a major diameter do measured between the crests 29. One or both of the diameters di, do may be constant or may vary along the length of the fastener 20.

The crests 29 may be tapered to facilitate self-tapping, or may be truncated and substantially flat. The crests 29 may be constant or may vary along the length of the thread 21. The thread 21 includes a depth measured from the root 28 to the crest 29. FIG. 12 includes the thread depth being consistent along the length the shank 22. The depth may also vary along the length as necessary. The thread 21 may also include the same or different angles and/or pitch along the length. FIG. 12 includes the thread angle and pitch being the same along the length of the thread 21.

A receptacle 26 may extend into the head 25 to receive a tool for applying torque to the fastener 20. The receptacle 26 may include a variety of shapes to receive a tool with a variety of drive types including but not limited to slotted, Phillips, hexagonal, Torx, spline drive, and double hex.

The cross-sectional shape of the head 25 may also vary, including but not limited to pan head, button, round, countersunk, and oval. The head 25 may further include the same size and shape as the shank 22. The cross-sectional shape of the shank 22 may be circular or may also be other shapes. The term diameter is again used and applies to these various shapes.

One or more self-tapping flutes 27 may be positioned at the distal tip 23. The flutes 27 are non-threaded and extend into the shank 22 to facilitate insertion and movement through the bone 100.

Fastener 20 also includes an interference section 72 that extends along a longitudinal section of the length. The interference section 72 includes a greater diameter than the diameter W' of the interference section 70 of the passage 40. This difference in size causes the interference section 72 to contact against and modify or be modified by the interference section 70 to create an interference fit between the fastener 20 and the implant 30. In one embodiment, just the thread 21 creates the interference section 72. Other embodiments include the central body of the shank 22 formed the interference section 72. The length L of the interference section 72 measured along the longitudinal axis L may vary.

Figure 13:
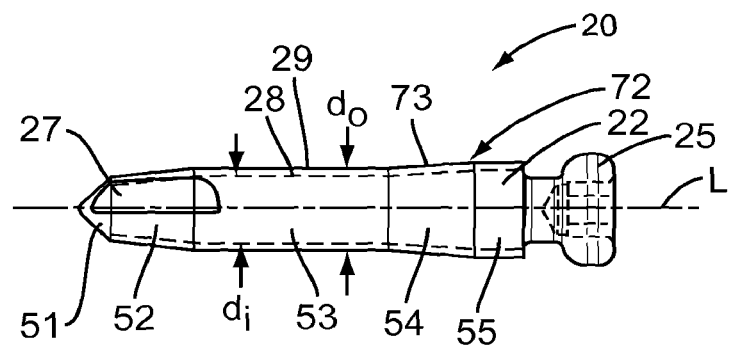
FIG. 13 is a side schematic view of the fastener of FIG. 12.

FIG. 13 illustrates a theoretical side view of the screw of FIG. 12. The dashed lines extending along the shank 22 illustrate the minor diameter di defined by the roots 28, and the solid lines 29 illustrate major diameter do defined by the crests 29. FIG. 13 includes the solid lines of the crests 29 parallel to the dashed lines of the roots 28 as the thread depth is the same along the length of the shank 22.

The fastener 20 includes one or more longitudinal sections 50 each extending along a length of the longitudinal axis L. The sections 50 may include constant or varying diameters di, do. A first section 51 extends inward from the distal tip 23. The fastener of FIG. 13 includes a first section 51 with a tapered shape that widens in a proximal direction away from the tip 23. The thread 21 may or may not extend along the first section 51. In one embodiment, the thread 21 begins along the first section 51. Second and fourth sections 52, 54 are positioned along the shank 22 and each includes a tapered shape that increases towards the proximal end of the fastener 20. The tapers may be the same or may be different. Sections 52, 54 each include a linear taper. Tapers may also be non-linear (i.e., curved taper). FIG. 13 includes the fourth section 54 with a sharper taper than the second section 52. Third and fifth sections 53, 55 each include constant diameters di, do along their lengths.

In this embodiment, the interference section 72 is formed by a portion of the fourth section 54 and the fifth section 55 in the fastener 20 of FIG. 13. Positioning a starting edge 73 (i.e., distal edge) of the interference section 72 facilitates modifying of one of the interference sections 70, 72.

FIGS. 14-16 illustrate the steps of attaching the implant 30 to a bone 100 with the fastener 20. The passage 40 in this embodiment features a wide first end 41 that tapers down and leads into the interference section 70. As illustrated in FIG. 14, the fastener 20 is inserted through the passage 40 with the distal tip 23 contacting against the bone 100. At this amount of insertion, the threads 21 are engaging the bone 100 but are not contacting against the sidewalls 43 of the passage 40. The interference section 72 of the fastener 20 is positioned away from the interference section 70 of the passage 40.

FIG. 15 illustrates the fastener 20 inserted a further distance into the bone 100. At this point of insertion, the threads 21 at the interference section 72 are in contact with the interference section 70. In this example, the implant 30 is constructed of a softer material than the fastener 20. The sidewalls 43 are solid and substantially smooth and not pre-tapped. As the fastener 20 is rotated and moved through the passage 40, the interference section 72 modifies the interference section 70 and creates an interference fit. The interference section 72 may be self-tapping as it cuts the sidewalls 43, or may be thread-forming as it deforms the sidewalls 43. The interference section 72 is distanced away from the head 25 for modifying to occur prior to the head 25 bottoming out in the passage 40.

FIG. 16 illustrates the fastener 20 fully inserted into the bone 100. The amount of insertion is controlled by the head 25 contacting against the passage 40. In this embodiment, the head 25 and passage 40 are configured for the head 25 to fit within and be recessed within the passage 40. The interference section 72 remains engaged with the interference section 70 with this contact forming the interference fit to prevent fastener 20 backout.

The embodiment of FIGS. 14-16 may also be used with the fastener 20 constructed of a softer material than the implant 30. As the fastener 20 moves through the passage 40, the interference section 72 of the fastener 20 is modified by the interference section 70. This may include just the thread 21 be modified as it moves past the interference section 70, or may also include modification of the main body of the shank 22.

Figure 17:
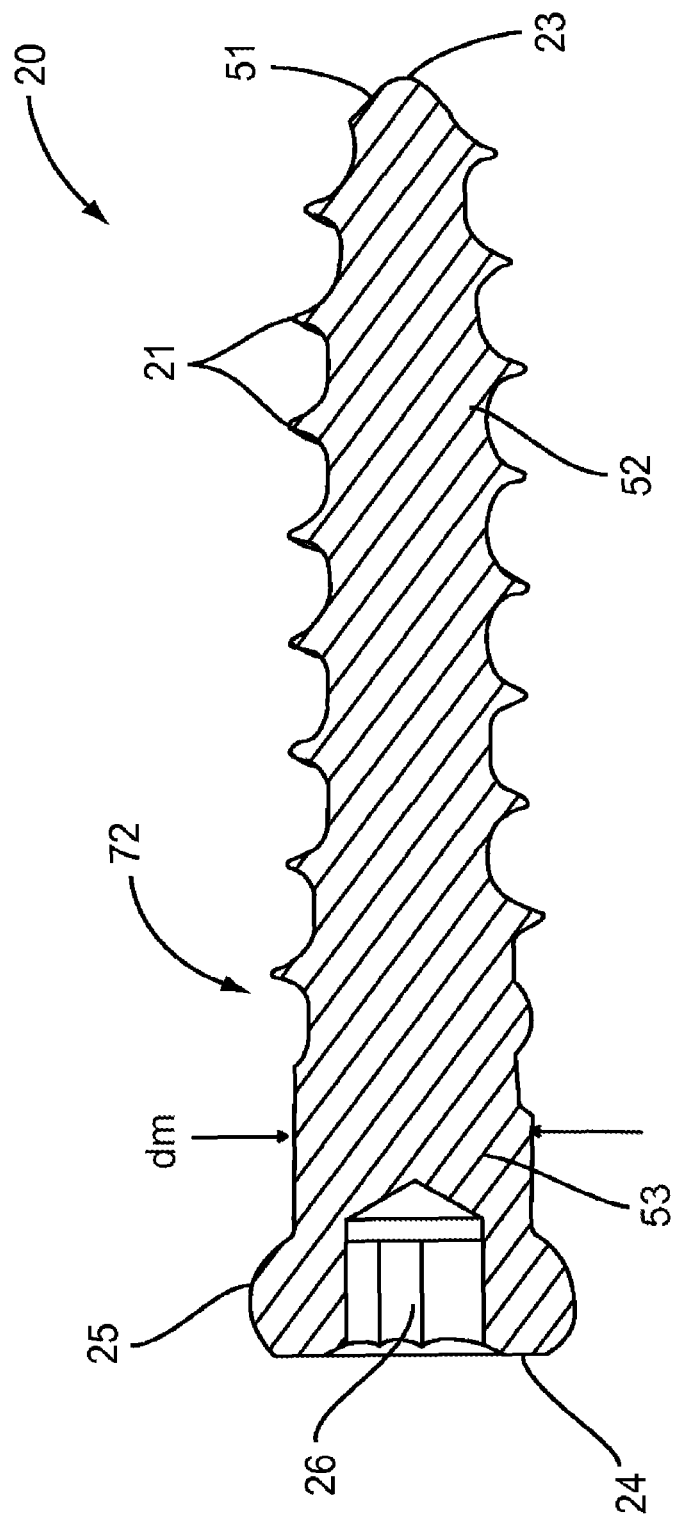
FIG. 17 is a sectional view of a fastener according to one embodiment.

FIG. 17 includes a fastener 20 with a first longitudinal section 51 that includes the distal tip 23, a second threaded longitudinal section 52, and a third longitudinal section 53 each being positioned distally from the head 25. The second longitudinal section 52 includes a gradually tapering shape with the diameters di, do increasing towards the proximal end. The interference section 72 is positioned at the proximal end of the second section 52. A thread 21 extends along the length of the section 52. Section 57 is positioned between the interference section 72 and a distal edge of the head 25. The longitudinal section 57 is non-threaded and includes a diameter dm that is smaller than the major diameter do of the interference section 72.

FIGS. 18-20 illustrate the steps of attaching the implant 30 to the bone 100 with this fastener 20. These steps include the fastener 20 constructed of a harder material than the implant 30. FIG. 18 includes the fastener 20 inserted a first amount with the first section 51 and a portion of the second section 52 extending into the bone 100. The diameter of the portion of the second section 52 within the passage 40 is smaller than the passage 40 with the thread 21 spaced from the sidewall 43.

FIG. 19 illustrates the fastener 20 inserted a greater distance into the bone 100. At this point of insertion, the interference section 72 contacts against and modifies the interference section 70. The sidewall 43 is solid and is not pre-tapped. The interference section 72 is spaced a distance from the head 25 to modify the interference section 70 prior to the head 25 being seated in the implant 30.

FIG. 20 illustrates the fastener 20 fully inserted into the bone 100. The head 25 is bottomed out in the passage 40 and in contact with the sidewall 43. Further, the interference section 72 has moved beyond the interference section 70. In this embodiment, the interference section 72 is moved beyond the second end 42 of the passage 40 and into the bone 100. The fastener 20 is prevented from backing out of the bone 100 as the threads 21 no longer align with the contours that were formed in the interference section 70. Therefore, any potential movement out of the bone 100 is prevented as the thread 21 on the interference section 72 contacts against the implant 30. FIG. 20 also illustrates that the longitudinal section 57 does not contact against the sidewall 43. In a similar arrangement as FIG. 20, the fastener 20 may be constructed such that the interference section 72 may move longitudinally beyond the interference section 70 but remain within the passage 40.

The embodiment of FIGS. 18-20 may also be performed with the implant 30 be constructed from a harder material than the fastener 20. The fastener 20 is modified as it is inserted through the passage 40. The interference section 72 is modified by the contact with the interference section 70.

Figure 21:
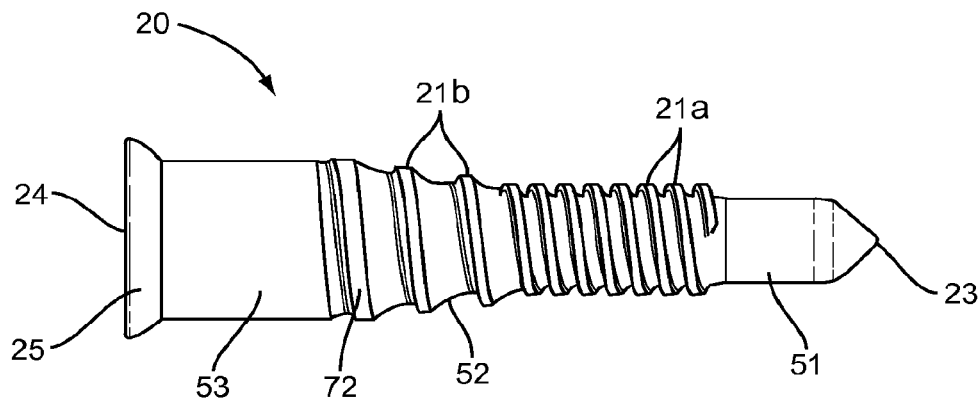
FIG. 21 is a side view of a fastener according to one embodiment.

Fasteners 20 may include other configurations to interact with the interference section 70 and attach the implant 30 to the bone 100. FIG. 21 includes a fastener 20 with a first thread 21a extending along a first section 51, and a second thread 21b extending along second and third sections 52, 53. The threads 21a, 21b may include one or more different aspects, including outer diameters, thread angle, and pitches. The interference section 72 is formed by a portion of the second section 52 and the third section 53. In this embodiment, the first thread 21a is configured to attach to the bone 100, and the second thread 21b is configured to engage with and modify or be modified by the interference section 70. Fasteners 20 may also include more than two different threads 21. Examples of multiple thread fasteners 20 are disclosed in US Patent Publication No. 2007/0233122 herein incorporated by reference in its entirety.

Figure 22:
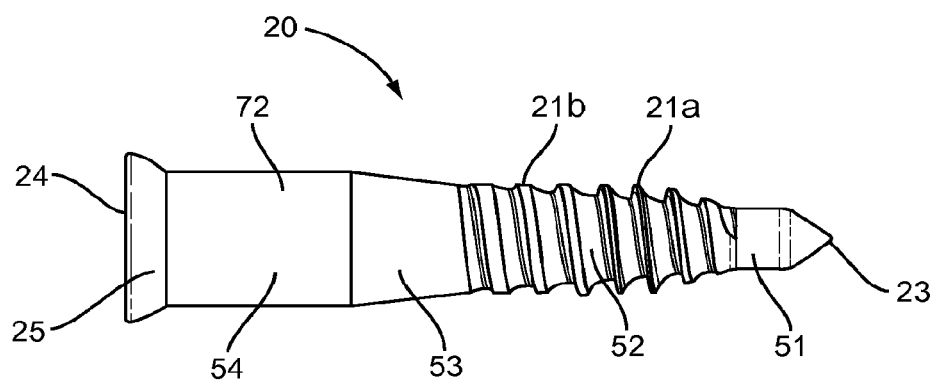
FIG. 22 is a side view of a fastener according to one embodiment.
Figure 23:
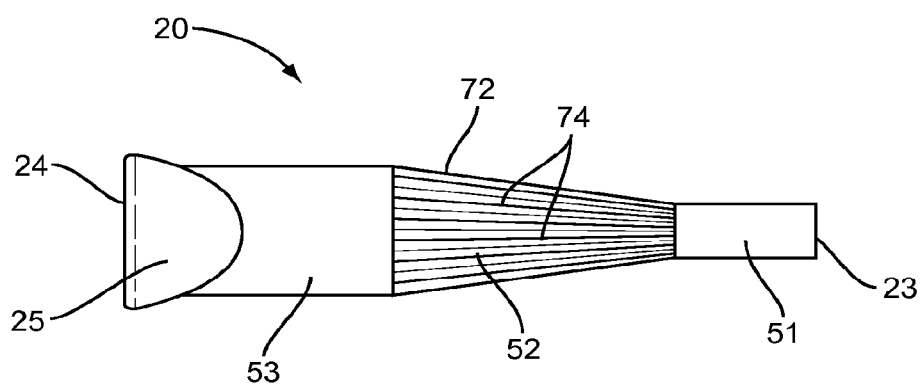
FIG. 23 is a side view of a fastener according to one embodiment.

The interference section 72 may also be formed along a non-threaded section of the fastener 20. FIG. 22 includes a fastener 20 with a first section 51, threaded second section 52, and non-threaded third and fourth sections 53, 54. The interference section 72 is formed by the fourth section 54 with the distal edge formed at the intersection of the third and fourth sections 53, 54. FIG. 23 includes a fastener 20 with the interference section 72 formed by the second section 52. A series of engagement features 74 are positioned in the second section 52. The engagement features 74 may include grooves that are cut into the main body of the shank 22. The grooves may be longitudinal, radial, or helical. Engagement features 74 may also include protrusions that extend outward from the surface of the main body of the shank 22. The engagement features 74 facilitate engagement with the interference section 70 and/or inhibit further rotation that could cause backout of the fastener 20. In a similar embodiment, one or more flutes 27 are positioned proximal to the interference section 72.

Figure 24:
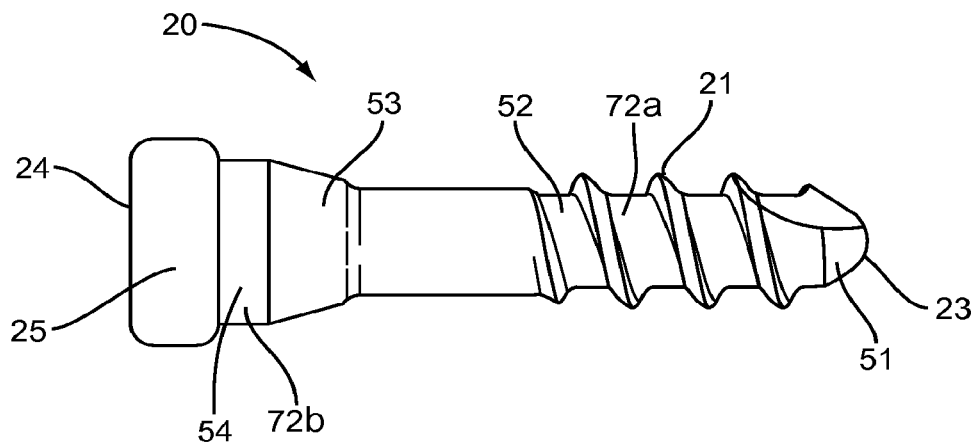
FIG. 24 is a side view of a fastener according to one embodiment.

Fastener 20 may also include multiple modifying sections 72 located along the length. FIG. 24 includes an embodiment with a first interference section 72a located along a second section 52, and a second interference section 72b located along the fourth section 54. The first interference section 72a includes a thread 21 and is sized to initially modify or be modified by the interference section 70. The second interference section 72b is positioned proximally from the first interference section 72a. The second interference section 72b is also sized to contact against the interference section 70. In this example, the second interference section 72b includes a larger diameter than the first interference section 72a.

During insertion of the fastener 20 into the passage 40, the first interference section 72a moves through the passage 40 and modifies or is modified by the interference section 70. Further insertion of the fastener 20 moves the second interference section 72b into the interference section 70 and results in further modification. The fastener 20 may include a size for a double interference fit with the first interference section 72a moving beyond the interference section 70 and modifying or being modified by the interference section 70 to prevent backout. The second interference section 72b may remain in the interference section 70 and form a second interference fit. The fastener 20 may further include more than two separate modifying sections 72.

The various fasteners 20 used to attach the implant 30 to the bone 100 may include different structures. The fasteners 20 described above include different combinations of these structures. The various interference sections 70, tapers, longitudinal sections 50, diameters di, do, threads 21, heads 25, tips 23, receptacles 26, etc. may be combined in a variety of different combinations within a fastener 20 depending upon the context of use and are included within the scope of the present application.

The modification of one of the interference sections 70, 72 creates the interference fit that prevents backout. The modification may include a self-tapping engagement as material is cut to form threads on the softer interference section 70, 72. The modification may also include thread-forming engagement caused by deformation of the softer interference section 70, 72. The modification may also include a variety of other deforming, cutting, and otherwise general altering of the softer interference section 70, 72. The modifications caused by the engagement between the sections 70, 72 are permanent.

The implants 10 may include more than one passage 40 and be attached to the bone 100 by more than one fastener 20. In these embodiments, at least one of the passages 40 includes an interference section 70 that is modified by a fastener 20. The other passages 40 may or may not include an interference section 70. Further, with implants 30 with multiple passages 40, each of the passages 40 may include the same or different structure. Likewise, the fasteners 20 may each be the same or one or more may be different.

The implants 30 may be attached to a variety of different bones 100 within the patient. These include the vertebrae as well as the long bone of the patient.

In one embodiment, the implant 30 is constructed of PEEK and the fastener 20 is constructed of titanium. The sidewalls 43 of the passage 30 are solid and non-threaded.

The implants 30 may be implanted within a living patient for the treatment of various spinal disorders. The implants 30 may also be implanted in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A medical device for treating a patient comprising:
    an implant comprising opposite superior and inferior surfaces that are each configured to engage vertebral tissue, the superior and inferior surfaces each extending between opposite side walls;
    a solid, non-threaded passage that extends through one of the sidewalls and the inferior surface of the implant without extending through the superior surface, the passage including a first interference section with a first diameter, the first interference section extending along an entire length of the passage, the first diameter being a constant diameter along the entire length of the passage;
    a fastener with an elongated shape and a distal end and a proximal end, the fastener including a second interference section located between the ends that includes a second diameter that is greater than the first diameter;
    one of the first and second interference sections constructed from a harder material and the other constructed from a softer material;
    a surface of the interference section constructed from the softer material being modified by insertion of the fastener into the passage to create an interference fit between the implant and the fastener.

2. The device of claim 1, wherein the passage has an angled orientation such that a first end of the passage is isolated to just within one of the sidewalls.

3. The device of claim 1, wherein
    the passage extends at an acute angle relative to the superior and inferior surfaces.

4. The device of claim 1, wherein the passage defines a longitudinal axis, the passage being symmetrical about the longitudinal axis and having a circular shape when viewed along the longitudinal axis.

5. The device of claim 1, wherein the fastener comprises a first longitudinal section that includes a distal tip at the distal end, a second threaded longitudinal section extending from the first longitudinal section and a third longitudinal section extending from the second longitudinal section, the third longitudinal section being positioned distally from a head of the fastener at the proximal end.

6. The device of claim 5, wherein the second longitudinal section has a gradually tapering shape with a diameter that increases toward the proximal end.

7. The device of claim 5, wherein the third longitudinal section is unthreaded and is positioned between the second interference section and a distal edge of the head.

8. The device of claim 5, wherein the third longitudinal section is unthreaded and has a major diameter that is less than that of the second interference section.

9. The device of claim 5, wherein the second longitudinal section has a maximum diameter that is less than the first diameter.

10. The device of claim 5, wherein the second and third longitudinal sections each have a maximum diameter that is less than the first diameter.

11. The device of claim 1, wherein the fastener includes a shaft comprising a distal portion including a thread form, a head having a maximum diameter that is greater than that of the shaft and an intermediate portion that extends from the thread form to the head, the distal portion comprising the second interference section, the intermediate portion being unthreaded.

12. The device of claim 11, wherein the maximum diameter of the head is greater than a maximum diameter of the intermediate portion.

13. A medical device for treating a patient comprising:
an implant comprising opposite superior and inferior surfaces that are each configured to engage vertebral tissue, the superior and inferior surfaces each extending between opposite side walls;
a passage that extends through one of the sidewalls and the inferior surface of the implant without extending through the superior surface, the passage including an interference section with solid non-threaded sidewalls, the interference section includes a first diameter, the interference section extending along an entire length of the passage, the first diameter being a constant diameter along the entire length of the passage;
a fastener with an elongated shape and a distal end and a proximal end, the fastener includes a modifying section located between the ends that includes a second diameter that is greater than the first diameter;
the fastener constructed from a harder material than the implant with the modifying section modifying the interference section during insertion of the fastener into the passage and creating an interference fit between the implant and the fastener.

14. The device of claim 13, wherein the modifying section includes a thread.

15. The device of claim 13, wherein the interference section is constructed from a material that is permanently modified by the modifying section.

16. The device of claim 13, wherein the fastener includes a head and a shank, the head including a head diameter that is greater than the shank and the second diameter, the modifying section being spaced away from the head towards the distal end.

17. The device of claim 16, wherein a first distance measured along a longitudinal axis of the fastener between a distal edge of the head and a proximal edge of the modifying section is greater than a second distance measured between first and second ends of the passage.

18. The device of claim 13, wherein the implant is constructed from PEEK.

19. A medical device for treating a patient comprising:
an implant comprising opposite superior and inferior surfaces that are each configured to engage vertebral tissue, the superior and inferior surfaces each extending between opposite side walls;
a fastener with a head positioned at an end of a shank, the fastener includes a modifying section located along the shank with a modifying section diameter larger than a remainder of the shank and smaller than the head;
a passage that extends through one of the sidewalls and the inferior surface of the implant without extending through the superior surface, the passage including an interference section with solid non-threaded sidewalls, an interference section diameter being smaller than the modifying section diameter, the interference section extending along an entire length of the passage, the interference diameter being a constant diameter along the entire length of the passage;
the fastener being constructed of a harder material than the passage;
a first distance measured along a longitudinal axis of the fastener between a distal edge of the head and a proximal edge of the modifying section being greater than a second distance measured along a longitudinal axis of the passage between a contact surface that receives the head.

20. The device of claim 19, wherein the modifying section is positioned inward from distal and proximal ends of the shank.

* * * * *

UNITED STATES PATENT AND TRADEMARK OFFICE
CERTIFICATE OF CORRECTION

| | | Page 1 of 1 |
|---|---|---|
| PATENT NO. | : 9,433,453 B2 | |
| APPLICATION NO. | : 14/751939 | |
| DATED | : September 6, 2016 | |
| INVENTOR(S) | : Melkent et al. | |

It is certified that error appears in the above-identified patent and that said Letters Patent is hereby corrected as shown below:

In the Specification

In Column 1, Line 8, delete "2009," and insert -- 2009, now Pat. No. 9,095,444, --, therefor.

In Column 9, Line 37, delete "passage 30" and insert -- passage 40 --, therefor.

Signed and Sealed this
Fifteenth Day of November, 2016

Michelle K. Lee
*Director of the United States Patent and Trademark Office*